United States Patent
Short et al.

(10) Patent No.: US 10,480,843 B2
(45) Date of Patent: Nov. 19, 2019

(54) ICE-MAKING MACHINE THAT UTILIZES CLOSED-LOOP HARVEST CONTROL WITH VIBRATIONAL FEEDBACK

(71) Applicant: MANITOWOC FOODSERVICE COMPANIES, LLC, New Port Richey, FL (US)

(72) Inventors: Daniel Lee Short, Manitowoc, WI (US); Christopher Greicar, Manitowoc, WI (US); Richard T. Miller, Manitowoc, WI (US); William Eugene Olson, Jr., Bellevue, WI (US); Brian Gerald Polly, Manitowoc, WI (US); John Phillip Myers, Manitowoc, WI (US)

(73) Assignee: MANITOWOC FOODSERVICE COMPANIES, LLC, New Port Richey, FL (US)

( * ) Notice: Subject to any disclaimer, the term of this patent is extended or adjusted under 35 U.S.C. 154(b) by 0 days.

(21) Appl. No.: 15/875,438

(22) Filed: Jan. 19, 2018

(65) Prior Publication Data

US 2019/0226739 A1    Jul. 25, 2019

(51) Int. Cl.
*F25C 1/12* (2006.01)
*G01N 29/02* (2006.01)

(52) U.S. Cl.
CPC ............... *F25C 1/12* (2013.01); *G01N 29/02* (2013.01); *F25C 2300/00* (2013.01);
(Continued)

(58) Field of Classification Search
CPC .......... F25C 2600/04; F25C 1/20; F25C 1/12; F25C 5/02; G01N 29/02
See application file for complete search history.

(56) References Cited

U.S. PATENT DOCUMENTS 3,411,309 A * 11/1968 Skrebowski ........... B01J 19/002
                                                   62/123
3,577,740 A *  5/1971 Kenworthy ............ B01D 9/005
                                                   62/72
(Continued)

FOREIGN PATENT DOCUMENTS

CN     101680693 A      3/2010
WO    2008144864 A1    12/2008

OTHER PUBLICATIONS

International Preliminary Report on Patentability dated Dec. 7, 2012 from corresponding International Patent Application No. PCT/US11/046298, 4 pages.
(Continued)

*Primary Examiner* — Filip Zec
(74) *Attorney, Agent, or Firm* — Ohlandt, Greeley, Ruggiero & Perle, LLP (57) ABSTRACT

There is provided a method that includes (a) controlling a vibrator to produce an acoustic wave in accordance with a signal that includes (i) an on-time during which a packet of pulses is generated, followed by (ii) an off-time during which no pulses are generated, and thus includes (iii) a frequency component, (b) receiving an electrical representation of the acoustic wave that has been detected from a body of water that is being frozen on a structure, (c) extracting, from the electrical representation, (i) the frequency component, and (ii) a magnitude of the frequency component, (d) recognizing that the magnitude of the frequency component exceeds a threshold value, thus yielding a recognition, and (e) issuing a command to remove the body of water from the structure, in response to the recognition. There is also provided a system that employs the method, and a storage device containing instructions for the method.

18 Claims, 6 Drawing Sheets

(52) U.S. Cl.
CPC ...... *F25C 2301/00* (2013.01); *F25C 2400/02* (2013.01); *F25C 2700/02* (2013.01)

(56) References Cited

U.S. PATENT DOCUMENTS

| | | | |
|---|---|---|---|
| 4,628,736 | A | 12/1986 | Kirby et al. |
| 4,697,254 | A | 9/1987 | Pridham |
| 4,843,827 | A * | 7/1989 | Peppers .................. F25C 1/12 62/73 |
| 5,627,310 | A | 5/1997 | Johnson |
| 6,328,467 | B1 * | 12/2001 | Keyhani ................ B64D 15/20 374/16 |
| 6,568,270 | B2 * | 5/2003 | Hongerholt ............ G01N 29/02 73/170.26 |
| 6,612,156 | B1 | 9/2003 | Hakimuddin |
| 6,678,209 | B1 | 1/2004 | Peng |
| 7,190,011 | B2 | 3/2007 | Aizawa et al. |
| 7,350,367 | B2 | 4/2008 | Matsiev et al. |
| 7,638,735 | B2 * | 12/2009 | Petrenko .................. F25C 1/12 219/200 |
| 7,765,814 | B2 | 8/2010 | Goldstein |
| 8,738,302 | B2 | 5/2014 | Tirumala et al. |
| 9,644,879 | B2 | 5/2017 | Broadbent |
| 2006/0150738 | A1 | 7/2006 | Leigh |
| 2006/0218945 | A1 | 10/2006 | Goldstein |
| 2007/0101752 | A1 * | 5/2007 | Broadbent ............... F25C 1/12 62/349 |
| 2008/0029245 | A1 | 2/2008 | Goldstein |
| 2008/0196429 | A1 * | 8/2008 | Petrenko ................... F25C 1/12 62/207 |
| 2010/0124142 | A1 | 5/2010 | Laugharn et al. |
| 2017/0089629 | A1 * | 3/2017 | Ji .............................. F25C 1/24 |

OTHER PUBLICATIONS

Chinese Office Action dated Aug. 14, 2013 for Chinese application No. 201110060600.3.
Chinese Office Action dated Aug. 23, 2013 for Chinese application No. 201110060547.7.
Japanese Office Action dated Feb. 25, 2014 for Japanese application No. 2013-523282.
International Search Report dated Nov. 30, 2011 for corresponding PCT application No. PCT/US2011/046298.
Written Opinion dated Nov. 30, 2011 for corresponding PCT application No. PCT/US2011/046298.
International Search Report dated Mar. 23, 2018 for PCT application No. PCT/US2018/014471.
Written Opinion dated Mar. 23, 2018 for PCT application No. PCT/US2018/014471.

* cited by examiner

ICE-MAKING MACHINE THAT UTILIZES CLOSED-LOOP HARVEST CONTROL WITH VIBRATIONAL FEEDBACK

BACKGROUND OF THE DISCLOSURE

1. Field of the Disclosure

The present disclosure relates to an ice-making machine, and more particularly, to a generation of an acoustic wave, and an analysis of the acoustic wave as it is propagating through a body of water in the ice-making machine. The analysis recognizes when the body of water is frozen, so that the body of water can be harvested, as ice, from the ice-making machine.

2. Description of the Related Art

The approaches described in this section are approaches that could be pursued, but not necessarily approaches that have been previously conceived or pursued. Therefore, the approaches described in this section may not be prior art to the claims in this application and are not admitted to be prior art by inclusion in this section.

For efficient operation of an ice-making machine, it is desirable to remove the ice, also known as harvesting the ice, soon after the ice has fully formed. Such harvesting of the ice allows for a new body of water to be introduced so that a new body of ice can be formed, thus maximizing the usage of the ice-making machine.

In the current state-of-the-art, several methods are used to sense when an ice-making machine evaporator is ready and "loaded" with sufficient ice for collection or "harvest". Some methods employed to sense a presence of ice use microswitch, capacitance, optical, or microphone-based technologies to detect a thickness of an ice-bridge between individual cubes of ice, while the ice is forming on an evaporator. Each of these methods suffer from a common drawback of "non-deterministic ice formation". Ice-maker water is pumped up and over the evaporator, and then allowed to fall, in a waterfall-like cascade, over a cooled evaporator into a collection trough sitting at the bottom of the water path. Because gravity and environmental vibration create "noise", these "water-ribbons" trace down the evaporator and freeze in random paths. Therefore, there are ordinarily no two ice-making cycles with the same ice formation pattern. Thus, it becomes difficult to determine at what point in the ice-making cycle enough ice has been built up on the evaporator to trigger the removal and collection, i.e., harvest, of that slab of ice. This leads to a problem of double-slabbing and an eventual freeze-up of the ice-maker, which further results in a need for thawing and/or service of the ice-making machine. This dilemma can be even more compounded by the fact that some operators prefer either thicker or thinner cubes of ice based on their application need, and can set a specific ice-bridge thickness for their ice-making machine.

Another technique for recognizing the readiness of the ice for harvesting is to monitor a magnitude of a mechanical vibration that is propagating through a body of water as the body of water is being frozen. At a point in time when the magnitude exceeds a predetermined threshold, the body of water is assumed to be adequately frozen, and so, is harvested. A possible drawback of this technique is that it does not distinguish between various possible sources of mechanical vibrations, and so, cannot determine whether the change is due to a change in acoustics of the ice-making machine or spurious acoustics in an ambient noise environment. Consequently, this technique does not necessarily initiate harvesting at a most optimum time, and therefore, the ice-making machine may be operating at a less than optimum level of efficiency.

It is an object of the present disclosure to provide a technique for harvesting ice in an ice-making machine at a time that optimizes the efficiency of the ice-making machine.

SUMMARY OF THE DISCLOSURE

There is provided a method that includes (a) controlling a vibrator to produce an acoustic wave in accordance with a signal that includes (i) an on-time during which a packet of pulses is generated, followed by (ii) an off-time during which no pulses are generated, and thus includes (iii) a frequency component, (b) receiving an electrical representation of the acoustic wave that has been detected from a body of water that is being frozen on a structure, (c) extracting, from the electrical representation, (i) the frequency component, and (ii) a magnitude of the frequency component, (d) recognizing that the magnitude of the frequency component exceeds a threshold value, thus yielding a recognition, and (e) issuing a command to remove the body of water from the structure, in response to the recognition. There is also provided a system that employs the method, and a storage device containing instructions for the method.

BRIEF DESCRIPTION OF THE DRAWINGS

A component or a feature that is common to more than one drawing is indicated with the same reference number in each of the drawings.

DESCRIPTION OF THE DISCLOSURE

The present disclosure provides a system and method to produce a vibrational signal and monitor vibrational feedback in an ice-making machine, and then using that vibrational feedback to influence control system state transitions to make programmatic decisions about when to initiate a harvest stage. The system operates by using a physical transducer, such as a piezo-electric device or vibrational motor, to provide vibrational energy to transmit an acoustic wave through the system's mechanical structure to an Ice Thickness Probe (ITP) microphone sensor. The ITP converts the acoustic wave energy to an electrical signal, and a filtering for a bandwidth of interest is performed. Finally, frequency bands of interest are passed to a microcontroller for analog, digital, and Fast Fourier Transformation (FFT)

signal processing by firmware/software components, which results in initiating the state transitions.

The present disclosure provides a solution to the "non-deterministic ice formation" by utilizing a closed-loop harvest control method for detecting the presence of ice. Double-slabbing is avoided by generating a signal from a microcontroller, or other state machine logic driver, into a mechanically coupled transducer as a freeze cycle begins, and then reading the ITP microphone, or other vibrational sensing device, for the presence of that known signal. If the expected signal appears, then it can be assumed that ice exists on the evaporator and needs to be removed prior to initiating any subsequent freeze cycles. Another, identical "Freeze-In" check is conducted three minutes into the freeze cycle as a secondary backup verification method. Additionally, the occurrence of freeze-ins is greatly reduced because ambient noise need not be sampled or averaged over long periods of time to "teach" the control system how to discern between environmental noise and the generated signal, or when the sensor is in contact with the ice-bridge during a freeze cycle. The harvest state is initiated only after the reception of a particular signal pattern that is unlikely to occur in an ambient environment.

Figure 1:
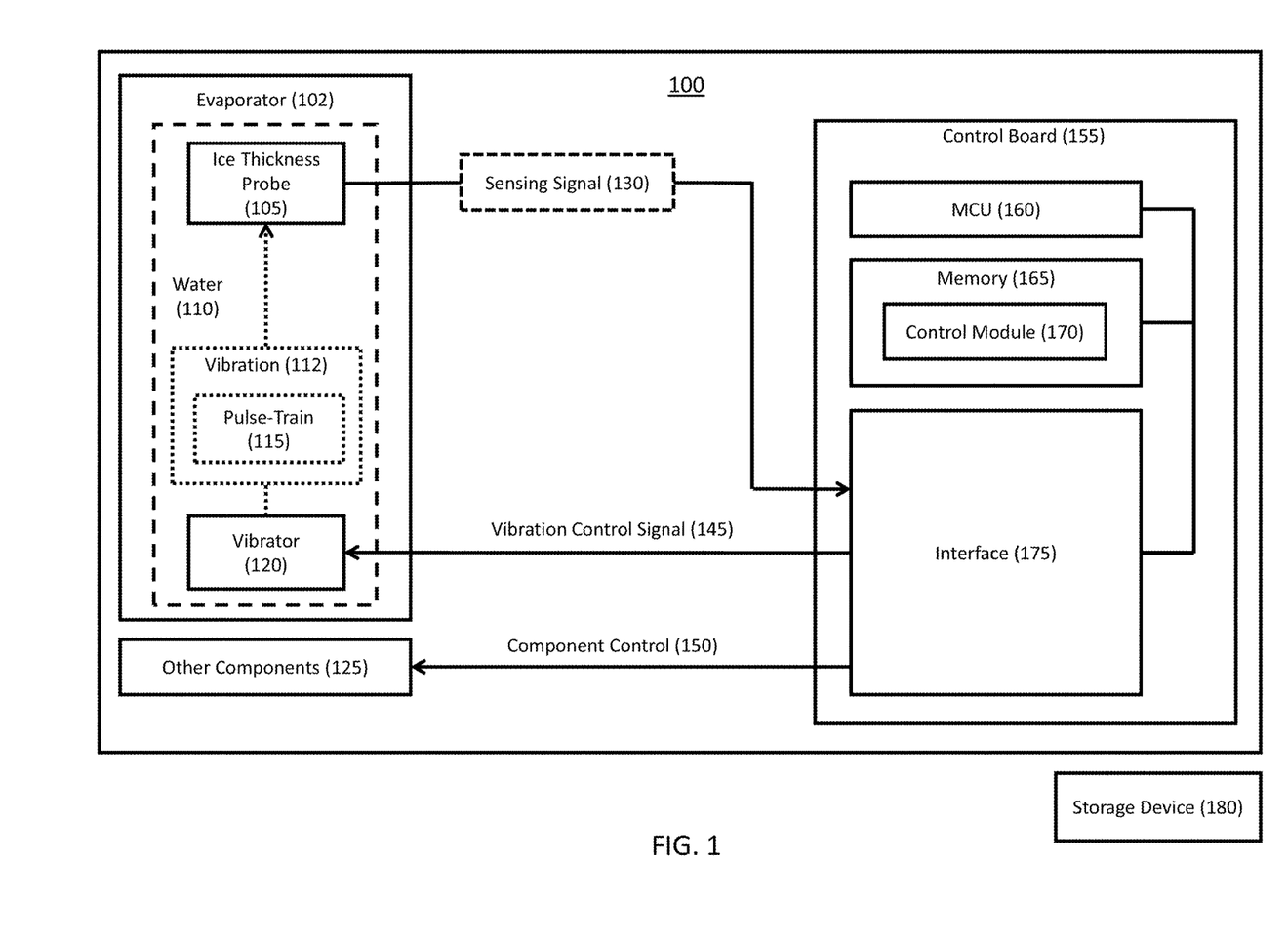
FIG. 1 is a functional block diagram of an ice-making system that utilizes closed-loop harvest control.

FIG. 1 is a functional block diagram of an ice-making system, i.e., system 100, that utilizes closed-loop harvest control. System 100 includes an evaporator 102, an ice thickness probe (ITP) 105, a control board 155, a vibrator 120, and other components 125.

Evaporator 102 is a structure that holds a body of water, i.e., water 110, that is being frozen.

Vibrator 120 is an electrical-to-mechanical transducer, for example, a vibration motor or a piezoelectric device. Vibrator 120 produces a vibration 112, and is situated so that vibration 112 propagates through water 110. Vibrator 120 may be located in water 110, or on a surface of evaporator 102, or elsewhere in system 100. In a practical implementation of system 100, vibrator 120 is encased in a vibration mounting assembly (not shown) that is situated in system 100 at a position to mechanically couple vibration 112 to water 110. Vibration 112 is in a form of a pulse-train 115, which is a particular signal pattern that propagates well through water 110 when water 110 is in the form of ice. Pulse-train 115 has a pattern that is deliberate and differentiable from machine noise frequencies and vibrations in an ambient environment of system 100, and thus maximizes signal-to-noise ratio. For example, pulse-train 115 can be a Pulse-Width-Modulated (PWM) and/or Frequency Modulated (FM) pulse-train.

ITP 105 is a mechanical-to-electrical transducer. ITP 105 senses vibration 112, converts it to an electrical signal, and produces a sensing signal 130. ITP 105 is situated so that it comes in contact with, or is in close proximity to, e.g., less than 0.5 inches, water 110 or evaporator 102.

Control board 155 produces a vibration control signal 145 that controls vibrator 120 to produce vibration 112 having pulse-train 115. Control board 155 receives and analyzes sensing signal 130 to determine whether sensing signal 130 includes pulse-train 115. The operation of generating pulse-train 115 in vibration 112, and analyzing pulse-train 115 in sensing signal 130, is referred to herein as closed-loop signal processing. If sensing signal 130 includes pulse-train 115, control board 155 concludes that water 110 is frozen, i.e., ice, and issues a command, i.e., a component control 150, to other components 125 to harvest the ice. Although component control 150 is shown as a single line and single command, in practice, it may include a plurality of lines and a plurality of commands. Thus, component control 150 represents the plurality of lines and the plurality of commands The closed-loop signal processing utilizes a non-random pattern of pulses for pulse-train 115 for closed-loop communication. The generation and receiving of pulse-train 115 indicates that there is a complete communication path through components of system 100. The detection of pulse-train 115 in sensing signal 130 may be used to indicate ice presence when it should be present, such as at the end of a freeze cycle, or as in the case of a fault, that the ice is not present when entering the freeze cycle from a pre-chill state.

Other components 125 represent other components of system 100 that are controlled by control board 155 to produce the ice. Other components 125 include, for example, valves for controlling flows of water onto evaporator 102, pumps for circulating water, and devices for releasing the ice from evaporator 102.

Control board 155 includes a microcontroller unit (MCU) 160, a memory 165, and an interface 175.

Interface 175 is an interface between components on control board 155 and other components in system 100. Interface 175 is an electronic circuit that enables control board 155 to receive sensing signal 130, and transmit vibration control signal 145 and component control 150.

MCU 160 is a computer processor, i.e., an electronic device configured of logic circuitry that responds to and executes instructions.

Memory 165 is a tangible, non-transitory, computer-readable storage device encoded with a computer program. In this regard, memory 165 stores data and instructions, i.e., program code, that are readable and executable by MCU 160 for controlling the operation of MCU 160. Memory 165 may be implemented in a random access memory (RAM), a hard drive, a read only memory (ROM), or a combination thereof. One of the components of memory 165 is control module 170.

While control module 170 is indicated as being already loaded into memory 165, it may be configured on a storage device 180 for subsequent loading into memory 165. Storage device 180 is a tangible, non-transitory, computer-readable storage device that stores control module 170 thereon. Examples of storage device 180 include (a) a compact disk, (b) a magnetic storage medium, (c) a read only memory, (d) an optical storage medium, (e) a hard drive, (f) a memory unit consisting of multiple parallel hard drives, (g) a universal serial bus (USB) flash drive, (h) a random access memory, and (i) an electronic storage device coupled to system 100 via a data network (not shown), e.g., the Internet.

Figure 2:
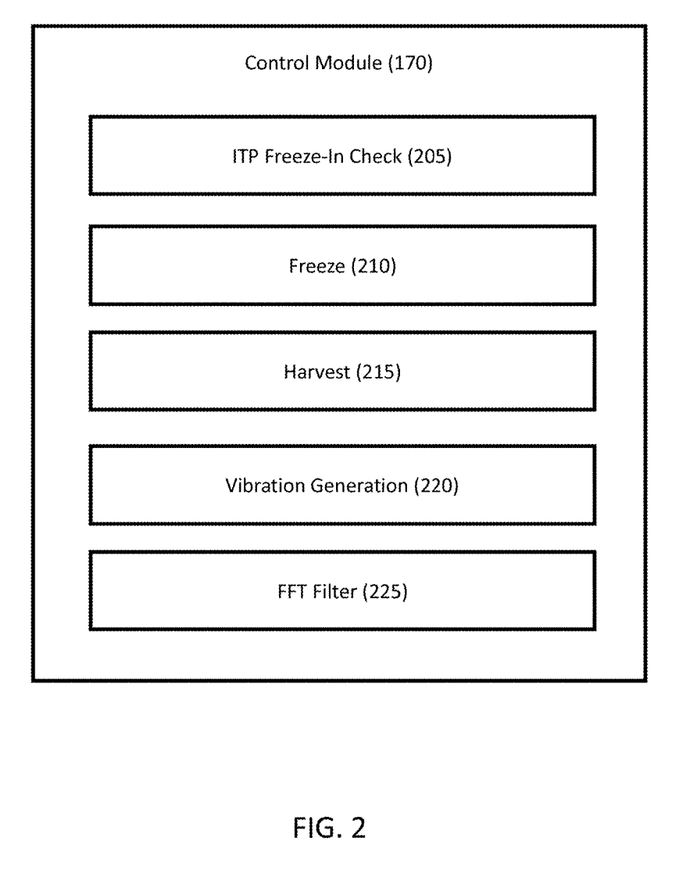
FIG. 2 is a block diagram of control module in the system of FIG. 1.

FIG. 2 is a block diagram of control module 170. Control module 170 includes several subordinate modules, namely, ITP Freeze-In Check 205, Freeze 210, Harvest 215, Vibration Generation 220, and FFT Filter 225. In the present document, when we describe operations being performed by control module 170 or its subordinate modules, the operations are actually being performed by MCU 160.

ITP Freeze-In Check 205 contains instructions for controlling MCU 160 to perform operations for a preliminary self-diagnostic check of system 100.

Freeze 210 contains instructions for controlling MCU 160 to perform operations for a freeze stage, also referred to as a freeze cycle, of system 100, i.e., to freeze water 110 to produce ice on evaporator 102.

Harvest 215 contains instructions for controlling MCU 160 to perform operations for a harvest stage, also referred to as a harvest cycle, of system 100, i.e., to harvest ice from evaporator 102.

Vibration Generation 220 contains instructions for controlling MCU 160 to perform operations to generate vibration control signal 145.

FFT Filter 225 contains instructions for controlling MCU 160 to perform an FFT and filtering of sensing signal 130. In this regard, FFT filter 225 conditions and compares frequencies being captured in sensing signal 130 in real-time, against an ambient noise field, to determine if pulse-train 115 is present in sensing signal 130.

Figure 3:
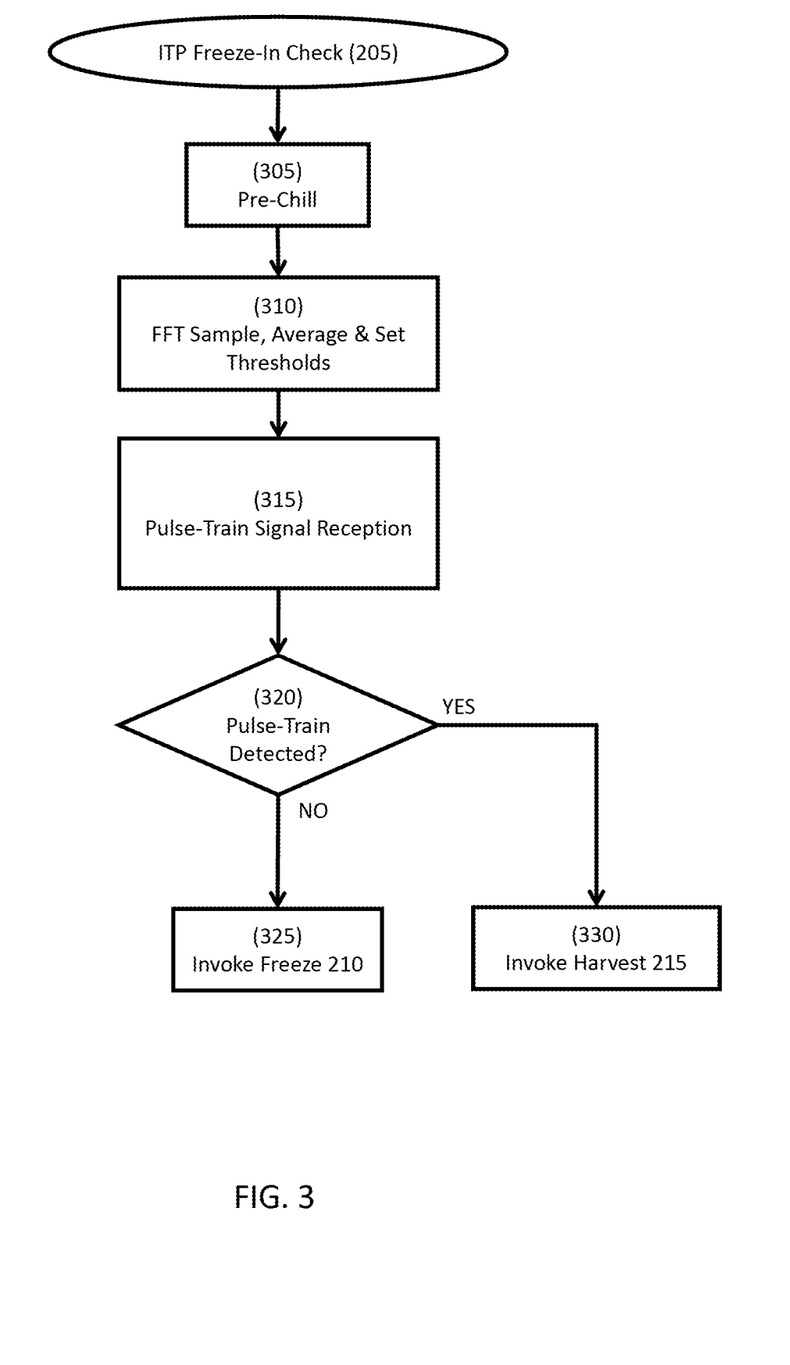
FIG. 3 is a flowchart of a routine that is performed by the control module of FIG. 2 for a preliminary self-diagnostic check of the system 100 of FIG. 1.

FIG. 3 is a flowchart of ITP Freeze-In Check 205. For sake of brevity, we refer to ITP Freeze-In Check 205 as process 205. Process 205 commences with operation 305.

In operation 305, process 205 performs a pre-chill of water 110. Operation 305 may have a duration of several minutes. From operation 305, process 205 proceeds to operation 310.

In operation 310, process 205 samples instantaneous FFT values of sensing signal 130, and frequency spectrum components of sensing signal 130 are recorded and averaged to establish an activation threshold above an ambient noise floor. From operation 310, process 205 proceeds to operation 315.

In operation 315, process 205 causes control board 155 to issue vibration control signal 145 to cause vibrator 120 to produce vibration 112 having pulse-train 115. Process 205 receives and analyzes sensing signal 130 to determine whether sensing signal 130 includes pulse-train 115. From operation 315, process 205 proceeds to operation 320.

If sensing signal 130 includes pulse-train 115, then water 110 is assumed to be frozen. However, since process 205 is performing a preliminary check of system 100, water 110 is not yet expected to be frozen, and ice should not be present.

In operation 320, if sensing signal 130 does not include pulse-train 115, i.e., a normal condition at this time, process 205 proceeds to operation 325. If sensing signal 130 includes pulse-train 115, i.e., unexpected presence of ice, process 205 advances to operation 330.

In operation 325, process 205 invokes Freeze 210.

In operation 330, process 205 invokes Harvest 215 for an immediate clearing of the ice from evaporator 102.

Figure 4:
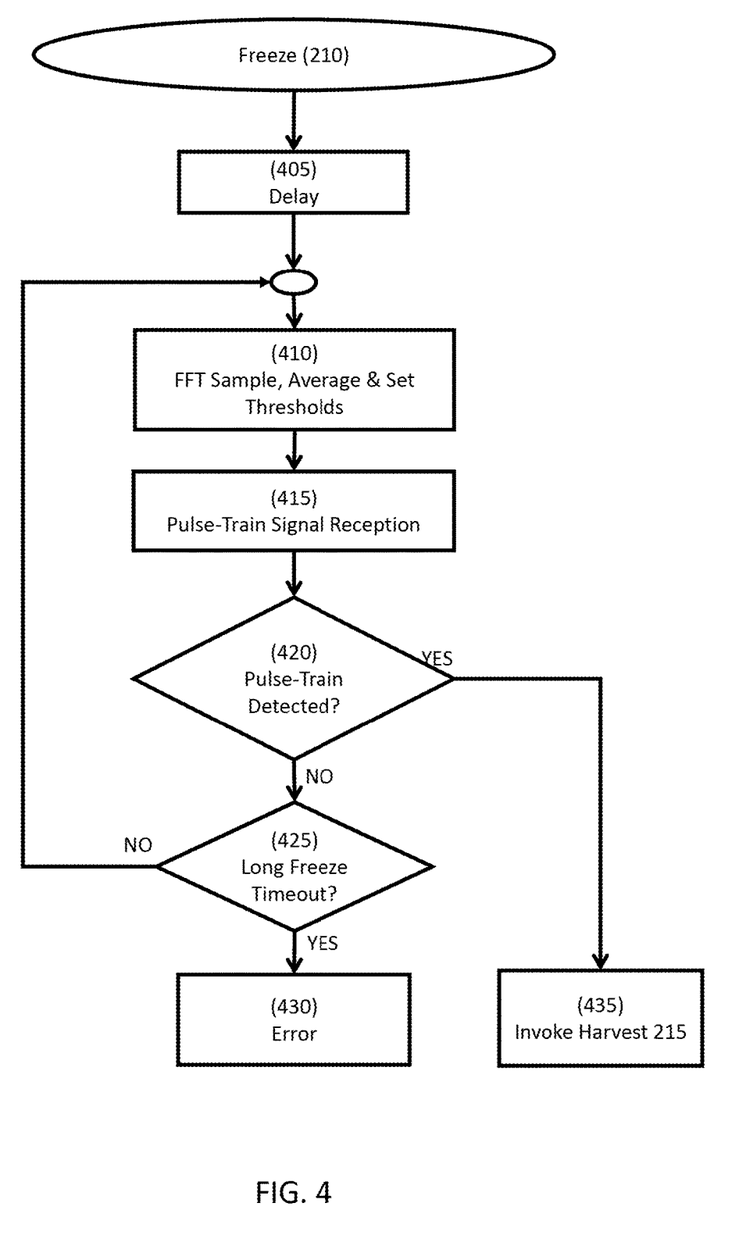
FIG. 4 is a flowchart of a routine that is performed by the control module of FIG. 2 to manufacture ice in the system of FIG. 1.

FIG. 4 is a flowchart of Freeze 210. Freeze 210 commences with operation 405.

In operation 405. Freeze 210 is in a delay to give water 110 an opportunity to freeze. This delay is included because if water 110 is not expected to be frozen, there will be no expectation that sensing signal 130 will include pulse-train 115, and so, there is no need to excite vibrator 120 to produce vibration 112. The delay avoids unnecessary use of vibrator 120, and thus prolongs the usable life of vibrator 120. The duration of the delay will depend on factors such as the physical size of evaporator 102 and the volume of water 110. In a practical embodiment, the delay will be several minutes. e.g., 6 minutes. Thus, several minutes are allowed to lapse after a commencement of Freeze 210, prior to generating vibration control signal 145. After completion of operation 405, Freeze 210 progresses to operation 410.

In operation 410, Freeze 210 samples instantaneous FFT values of sensing signal 130, and frequency spectrum components of sensing signal 130 are recorded and averaged to establish an activation threshold above an ambient noise floor. From operation 410, Freeze 210 proceeds to operation 415.

In operation 415, Freeze 210 causes control board 155 to issue vibration control signal 145 to cause vibrator 120 to produce vibration 112 having pulse-train 115. Freeze 210 receives and analyzes sensing signal 130 to determine whether sensing signal 130 includes pulse-train 115, and whether one or more of its frequency spectrum components has a magnitude that is greater than or equal to the activation threshold. From operation 415, Freeze 210 proceeds to operation 420.

In operation 420, if sensing signal 130 includes pulse-train 115, and if one or more of its frequency spectrum components has a magnitude that is greater than or equal to the activation threshold, then water 110 is assumed to be frozen, and Freeze 210 advances to operation 435. If sensing signal 130 does not include pulse-train 115, or if the magnitude(s) of its frequency component(s) is/are not greater than or equal to the activation threshold, then water 110 is assumed to not yet be frozen, and Freeze 210 proceeds to operation 425.

In operation 425, Freeze 210 performs a cumulative time check to determine whether a long freeze timeout has occurred. If water 110 has not frozen after some reasonable period of time, i.e., a timeout period, system 100 is assumed to have a fault. The timeout will occur in a case where system 100 has failed to produce ice before a termination of the timeout period. If the timeout has not occurred, i.e., normal operation, Freeze 210 loops back to operation 410. If the timeout has occurred, i.e., an indication of a possible error, Freeze 210 proceeds to operation 430.

In operation 430, Freeze 210 performs an error processing routine.

In operation 435, Freeze 210 invokes Harvest 215 for a clearing of the ice from evaporator 102.

FIGS. 3 and 4 illustrate a program flow for a preferred embodiment of system 100. However, there may be many other ways to utilize knowledge about "ice presence". One such possible use is to store the trailing ten freeze-times and use that information to establish a mean, median, and standard deviation for the specific machine model's freeze-times; given its current environment and water temperature. The storage and use of these statistics can lead to a probabilistic prediction of the most optimized use of the "modulated off-time" (e.g., see FIG. 5, off-time 510, and FIG. 6, off-times 610 and 610A), which can further save the life of vibrator 120. This method provides a way of targeting the most probable elapsed time wherein the ice will typically be ready to harvest.

Referring again to FIG. 1, interface 175 includes a low-pass filter (not shown) for sensing signal 130. In a practical embodiment, sensing signal 130 is largely centered around fundamental and harmonic vibrations near 1 kHz, and the value of a roll-off frequency ($f_c$) of the low-pass filter is mathematically calculated to be 1.592 kHz. This value represents the −3 dB roll-off frequency, and so, the highest input frequency for sensing signal 130 is chosen at 1 kHz, which is a frequency not often found in the environment as a naturally occurring noise, or radiating from any other 50/60 Hz rotational or electromagnetic noise sources.

In a practical implementation of system 100, FFT magnitudes of interest have been identified and chosen to match the response curve of ITP 105. Based on empirical data, the fundamental frequency used for pulse-train 115 is approximately 26 kHz-52 kHz. This frequency spectrum delivers a satisfactory 1 kHz input signal response at control board 155, i.e., in sensing signal 130.

The FFT frequency magnitudes associated with 50 Hz, 60 Hz, 100 Hz, 120 Hz, 150 Hz, 180 Hz, 200 Hz, 240 Hz, and 1 kHz are used to indicate the presence of pulse-train 115. For control board 155 to recognize sensing signal 130 as having pulse-train 115, pulse-train spectral components must be present in sensing signal 130.

In a practical implementation, magnitudes of the pulse-train spectral components are required to be above the average of the last 5 FFT samples, plus an additional marginal threshold value. The 1 kHz signal, and any two of the remaining frequencies identified above, must be present and above their respective marginal threshold values.

In a preferred embodiment of system 100, vibrator 120 is a button-style haptic vibration motor. It is chosen because of its good voltage-to-frequency vibration relationship, low current, low physical profile, and high values of Grms output power developed. In this preferred embodiment, vibrator 120 produces vibration 112 by an Eccentric Rotating Mass (ERM) technology, spinning @11000 RPM.

Another embodiment of vibrator 120 is a piezoelectric ceramic disk, which offers good generation of ultrasonic vibrations out of the ranges of normal human hearing. The advantage to the use of such a device within an ice-making machine lies in the ice-making machine's ability to perform harvest control functions without the customer's awareness. This is extremely important in units with remote condensing options, or where silent operation is desirable (e.g., a hospital recovery floor, or an under-counter open-bar). If piezoelectric devices are used, then orientation and location to a corresponding ITP 105 becomes very important; as piezoelectric devices can have very small values of vibrational amplitude displacement at the higher frequencies, and as such can be easily dampened by mounting methodologies.

To provide an appropriate level of vibrational force, vibrator 120 is encased within a vibrator mounting assembly (not shown) that is formed into a unibody wire harness/motor assembly (not shown) and then mounted in system 100 to deliver average vibrational acceleration forces from 1 $G_{rms}$ to 3 $G_{rms}$ at ITP 105.

A favorable balance between ease-of-installation, serviceability, and un-obstructed, i.e., minimally-dampened, distance to evaporator 102, leads to three primary means of securing the mounting assembly. Methods that tend to broadly generalize the techniques involved are screw-in, bracketed, and evaporator-direct conduction. However, the preferred embodiment uses a screw-in conduction method in which the mounting assembly is tightly coupled to a metal surface of system 100 using a threaded fastener and a molded plastic housing, in or upon which vibrator 120 is firmly mounted or affixed. This configuration transfers a maximal amount of energy, and ensures that vibration 112 is as quiet as is possible.

The preferred embodiment of ITP 105 is an input vibration sensing system that makes use of an electret (condenser) microphone responsive to acoustic frequencies in the audible 100-20 kHz spectrum. Vibration 112 is sensed and then transformed into sensing signal 130. Although this preferred embodiment makes use of an electret microphone as the primary transducing medium, it is by no means the only method which can be used as ITP 105. Other devices such as an accelerometer may be even more aptly suited to the task.

The primary transducing element in ITP 105 uses a Field Effect Transistor (FET) as the small signal amplifier, and is provided with a DC biasing voltage. A 0.1 micro-Farad coupling capacitor is used to pass a small signal representation of vibration 112, and thus pulse-train 115, as sensing signal 130 onto control board 155.

Figure 5:
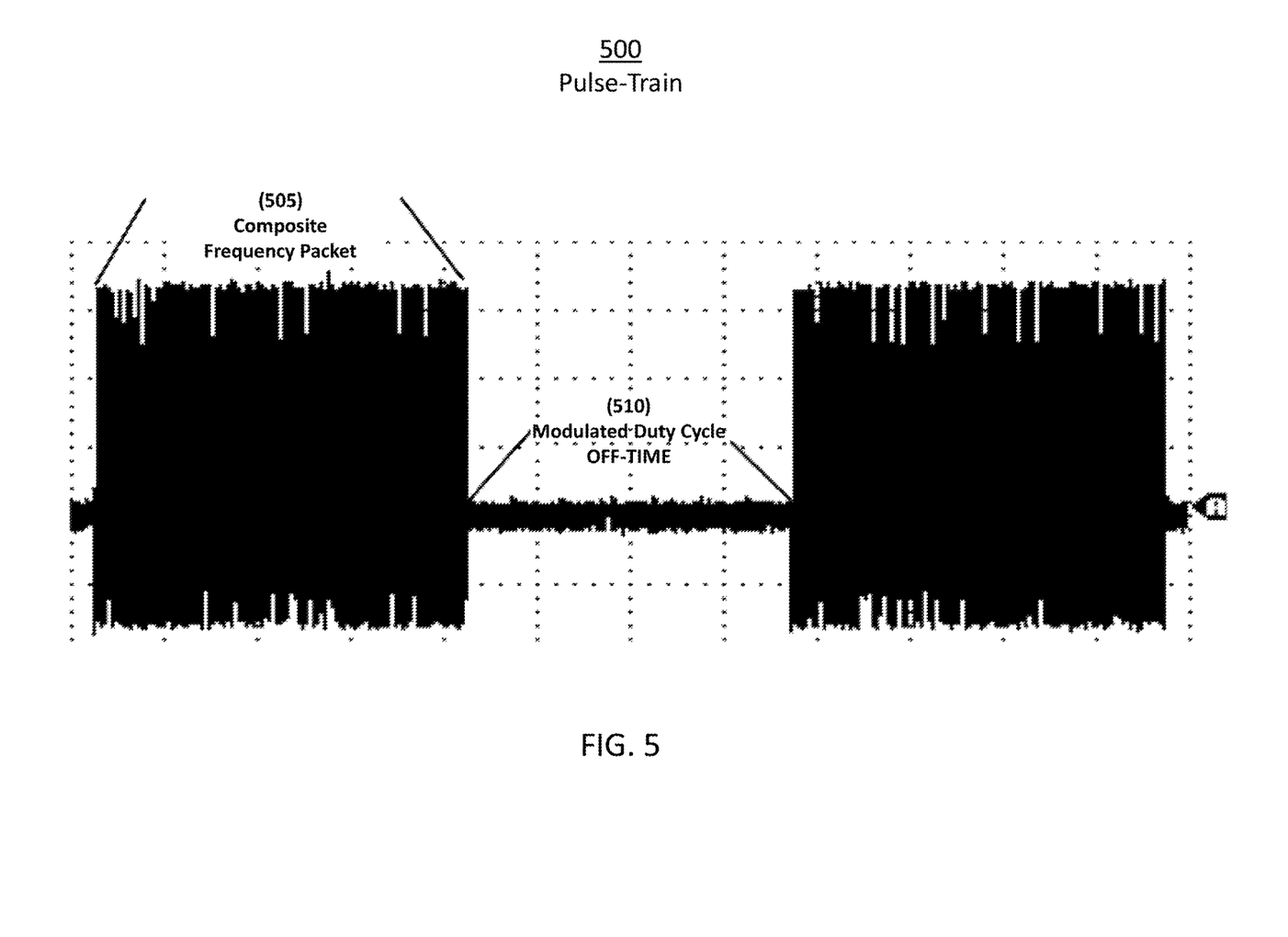
FIG. 5 is a graphical representation of an exemplary version of a pulse-train that is employed by the control module of FIG. 2.

FIG. 5 is a graphical representation of an exemplary version of pulse-train 115, designated herein as pulse-train 500. Pulse-train 500 has a pattern that is deliberate and differentiable from machine noise frequencies and vibrations in an ambient environment of system 100. In this regard, pulse-train 500 includes a composite frequency packet, i.e., packet 505, which is an "on-time", followed by a modulated duty cycle "off-time", i.e., off-time 510. Packet 505 consists of many one-second, mixed-frequency blocks, which are chosen to create an optimal frequency response in ITP 105, or to maximize an amplitude of sensing signal 130. Packet 505 has a duration of approximately 8 seconds, and is repeated after off-time 510.

Alternating packet 505 and off-time 510 establishes a polling time that is configurable to optimize the detection of ice at ITP 105, based on any unique machine model or efficiency parameters. Pulse-train 500 can be recurring, i.e., where packet 505 and off-time 510 are periodically repeated, or in the alternative, the duration of off-time 510 can be changed.

Figure 6:
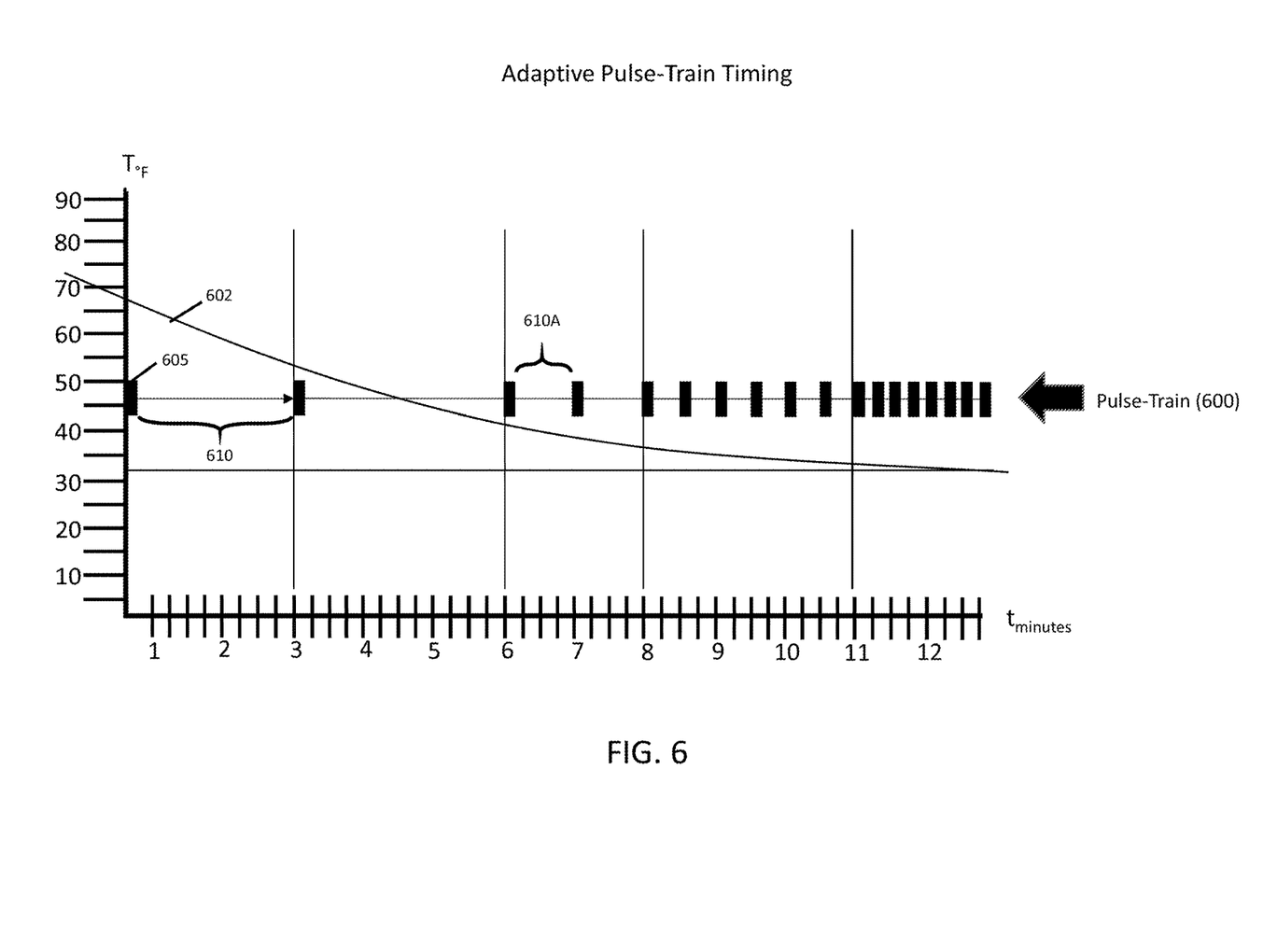
FIG. 6 is a graphical representation of another exemplary version of a pulse-train that is employed by the control module of FIG. 2.

FIG. 6 is a graphical representation of another exemplary version of pulse-train 115, designated herein as pulse-train 600, as system 100 progresses through Freeze 210. Pulse-train 600 has a pattern that is deliberate and differentiable from machine noise frequencies and vibrations in an ambient environment of system 100. Pulse-train 600 includes a composite frequency packet, i.e., packet 605, which is an "on-time", followed by a modulated duty cycle "off-time", i.e., off-time 610. Packet 605 has a duration of approximately 8 seconds, and is repeated after off-time 610. Packet 605 consists of many one-second, mixed-frequency blocks, which are chosen to create an optimal frequency response in ITP 105, or to maximize an amplitude of sensing signal 130.

As system 100 progresses through Freeze 210, the temperature (represented by a line 602) of water 110 can be used to model and subsequently drive the need for a specific interval of off-time 610; while simultaneously serving as an indicator of how close system 100 should be to executing Harvest 215. Since there is a minimal chance of water 110 freezing to evaporator 102 at temperatures above 32° F. (0° C.), system 100 does not benefit by any attempt to detect the presence of ice during that time interval (see operation 405). Pulse-train 600 is a preferred pulse-train timing sequence that is designed to match the physics of the formation of ice, as well as affording an added benefit of conserving vibrator 120's useful life by using vibrator 120 less often. As Freeze 210 progresses, durations of off-time 610 are reduced. For example, off-time 610 has a duration of greater than 2-minutes, and a subsequent off-time, e.g., off-time 610A, has a duration of less than 2-minutes. The utilization of pulse-train 600, and in particular the reduction of the duration of the off-time as Freeze 210 progresses, is an example of Adaptive Pulse-Train Timing.

In Freeze 210, during operation 405, ITP Freeze-In Check 205 is performed as a diagnostic, and then again at the 3-minute mark. These two checks are not expected to sense the presence of ice, but rather to ensure that no ice remains on evaporator 102 from previously failed harvest attempts. Once the 6-minute mark is passed, packet 605 is initiated, but at a 1-minute interval, since there is a relatively low probability of finding ice this early in the cycle. This one-minute pattern repeats until the 8-minute mark, at which point the interval decreases to once every 30 seconds. There is an increased probability of finding ice between 8 and 11 minutes, so the pattern of every thirty seconds continues until the 11-minute mark is reached. From this point forward in time, the temperature of water 110 is most near the freezing point, and this fact indicates that the ice-making machine has reached the point in time where it is most likely that ice will soon be in contact with P 105. For this reason, the pulse-train "Off-Time" is decreased even further to once every 15 seconds, where it continues until either the presence of ice is sensed, or the long freeze timeout in operation 425 has expired. Thus, vibration control signal 145 can generate pulse-train 600, where packet 605 is recurring, and the off-time of pulse-train 600 is reduced in duration as Freeze 210 progresses.

Thus, control board 155, and more specifically MCU 160, performs a method that includes:

(a) controlling vibrator 120, via vibration control signal 145, to produce vibration 112 in accordance with pulse-train 115, i.e., a signal that includes (i) an on-time during which a packet of pulses is generated, followed by (ii) an off-time during which no pulses are generated, and thus includes (iii) a frequency component;

(b) receiving sensing signal 130, i.e., an electrical representation of the acoustic wave that has been detected by ITP 105 from water 110, as water 110 is being frozen on evaporator 102;

(c) extracting, from sensing signal 130, (i) the frequency component, and (ii) a magnitude of the frequency component;

(d) recognizing that the magnitude of the frequency component exceeds a threshold value; and (e) issuing component control 150 to remove water 110, i.e., ice, from evaporator 102 when the magnitude of the frequency component exceeds the threshold value.

The techniques described herein are exemplary, and should not be construed as implying any particular limitation on the present disclosure. It should be understood that various alternatives, combinations and modifications could be devised by those skilled in the art. For example, steps associated with the processes described herein can be performed in any order, unless otherwise specified or dictated by the steps themselves. The present disclosure is intended to embrace all such alternatives, modifications and variances that fall within the scope of the appended claims.

The tell is "comprises" or "comprising" are to be interpreted as specifying the presence of the stated features, integers, steps or components, but not precluding the presence of one or more other features, integers, steps or components or groups thereof The terms "a" and "an" are indefinite articles, and as such, do not preclude embodiments having pluralities of articles.

What is claimed is:

1. A method comprising:
controlling a vibrator in an ice-making system to produce an acoustic wave in accordance with a signal having a pattern that includes (i) an on-time during which a packet of pulses is generated, followed by (ii) an off-time during which no pulses are generated, and thus includes (iii) a frequency component, wherein said pattern is differentiable from machine noise frequencies and vibrations in said ice-making system, and wherein said on-time is recurring, and said off-time is reduced in duration as said method progresses;
receiving an electrical representation of said acoustic wave that has been detected from a body of water that is being frozen on a structure in said ice-making system;
extracting, from said electrical representation, (i) said frequency component, and (ii) a magnitude of said frequency component;
recognizing that said magnitude of said frequency component exceeds a threshold value, thus yielding a recognition; and
issuing a command to remove said body of water from said structure, in response to said recognition.

2. The method of claim 1, wherein said signal is recurring.

3. The method of claim 1, wherein said method is performed in said ice-making system during a freeze cycle, and further includes, prior to said controlling, allowing several minutes to lapse after a commencement of said freeze cycle.

4. The method of claim 1, wherein said magnitude of said frequency component exceeding said threshold value occurs when said body of water has frozen to ice.

5. The method of claim 1, wherein said vibrator is situated at a location selected from the group consisting of (a) in said body of water, and (b) on a surface of said structure.

6. The method of claim 1, wherein said vibrator comprises a device selected from the group consisting of a haptic vibration motor, and a piezoelectric ceramic disk.

7. An ice-making system comprising:
a structure that holds a body of water that is being frozen;
a vibrator that produces an acoustic wave;
a detector that detects said acoustic wave propagating through said body of water, and produces an electrical representation of said acoustic wave; and
a controller configured to perform a method that includes operations of:
controlling said vibrator to produce said acoustic wave in accordance with a signal having a pattern that includes (i) an on-time during which a packet of pulses is generated, followed by (ii) an off-time during which no pulses are generated, and thus includes (iii) a frequency component, wherein said pattern is differentiable from machine noise frequencies and vibrations in said ice-making system, and wherein said on-time is recurring, and said off-time is reduced in duration as said method progresses;
receiving said electrical representation of said acoustic wave;
extracts, from said electrical representation, (i) said frequency component, and (ii) a magnitude of said frequency component;
recognizing that said magnitude of said frequency component exceeds a threshold value, thus yielding a recognition; and
issuing a command to remove said body of water from said structure, in response to said recognition.

8. The ice-making system of claim 7, wherein said signal is recurring.

9. The ice-making system of claim 7, wherein said operations are performed during a freeze cycle, and said operations further include, prior to said controlling, allowing several minutes to lapse after a commencement of said freeze cycle.

10. The ice-making system of claim 7, wherein said magnitude of said frequency component exceeding said threshold value occurs when said body of water has frozen to ice.

11. The ice-making system of claim 7, wherein said vibrator is situated at a location selected from the group consisting of (a) in said body of water, and (b) on a surface of said structure.

12. The ice-making system of claim 7, wherein said vibrator comprises a device selected from the group consisting of a haptic vibration motor, and a piezoelectric ceramic disk.

13. A storage device that is non-transitory and comprises instructions that are readable by a processor to cause said processor to perform a method that includes operations of:

controlling a vibrator in an ice-making system to produce an acoustic wave in accordance with a signal having a pattern that includes (i) an on-time during which a packet of pulses is generated, followed by (ii) an off-time during which no pulses are generated, and thus includes (iii) a frequency component, wherein said pattern is differentiable from machine noise frequencies and vibrations in said ice-making system, and wherein said on-time is recurring, and said off-time is reduced in duration as said method progresses;

receiving an electrical representation of said acoustic wave that has been detected from a body of water that is being frozen on a structure in said ice-making system;

extracting, from said electrical representation, (i) said frequency component, and (ii) a magnitude of said frequency component;

recognizing that said magnitude of said frequency component exceeds a threshold value, thus yielding a recognition; and issuing a command to remove said body of water from said structure, in response to said recognition.

14. The storage device of claim 13, wherein said signal is recurring.

15. The storage device of claim 13, wherein said operations are performed during a freeze cycle, and further include, prior to said controlling, allowing several minutes to lapse after a commencement of said freeze cycle.

16. The storage device of claim 13, wherein said magnitude of said frequency component exceeding said threshold value occurs when said body of water has frozen to ice.

17. The storage device of claim 13, wherein said vibrator is situated at a location selected from the group consisting of (a) in said body of water, and (b) on a surface of said structure.

18. The storage device of claim 13, wherein said vibrator comprises a device selected from the group consisting of a haptic vibration motor, and a piezoelectric ceramic disk.

* * * * *